(12) United States Patent
Schwarz et al.

(10) Patent No.: US 8,001,826 B2
(45) Date of Patent: Aug. 23, 2011

(54) METHODS AND APPARATUS FOR HIGH FREQUENCY IMPACT TESTING

(75) Inventors: Dwight Schwarz, Sahuarita, AZ (US);
Mark J. Kocan, Tucson, AZ (US)

(73) Assignee: Raytheon Company, Waltham, MA (US)

( * ) Notice: Subject to any disclaimer, the term of this patent is extended or adjusted under 35 U.S.C. 154(b) by 200 days.

(21) Appl. No.: 12/472,124

(22) Filed: May 26, 2009

(65) Prior Publication Data
US 2010/0300177 A1 Dec. 2, 2010

(51) Int. Cl.
*G01M 7/00* (2006.01)

(52) U.S. Cl. ...................................... 73/12.05

(58) Field of Classification Search ...... 73/12.01–12.14, 73/12.05–12.06, 12.13
See application file for complete search history.

(56) References Cited

U.S. PATENT DOCUMENTS

| | | | | |
|---|---|---|---|---|
| 4,640,120 A | * | 2/1987 | Garritano et al. | 73/12.13 |
| 4,776,202 A | * | 10/1988 | Brar et al. | 73/12.13 |
| 5,247,835 A | * | 9/1993 | Howell | 73/12.01 |
| 5,364,596 A | * | 11/1994 | Magnussen et al. | 422/515 |
| 5,535,627 A | * | 7/1996 | Swanson et al. | 73/597 |
| 5,656,017 A | * | 8/1997 | Keller et al. | 601/108 |
| 6,138,501 A | * | 10/2000 | Rastegar | 73/82 |
| 6,240,766 B1 | * | 6/2001 | Cawley | 73/12.01 |

* cited by examiner

*Primary Examiner* — Max Noori
(74) *Attorney, Agent, or Firm* — Ingrassia Fisher & Lorenz, P.C.

(57) ABSTRACT

An impact testing system for determining the shock response of a test structure includes a mass (e.g., a spherical steel ball) and a potential energy storage system (e.g., a spring-loaded mechanism) configured to store mechanical energy and, upon actuation, release the stored mechanical energy in the form of kinetic energy. A hold-and-release mechanism (such as a permanent magnet) is configured to releasably couple the mass to the potential energy storage system and impart linear momentum to the mass in connection with the kinetic energy such that the mass impinges upon the test structure. The shock response can then be determined and displayed to a user.

19 Claims, 3 Drawing Sheets

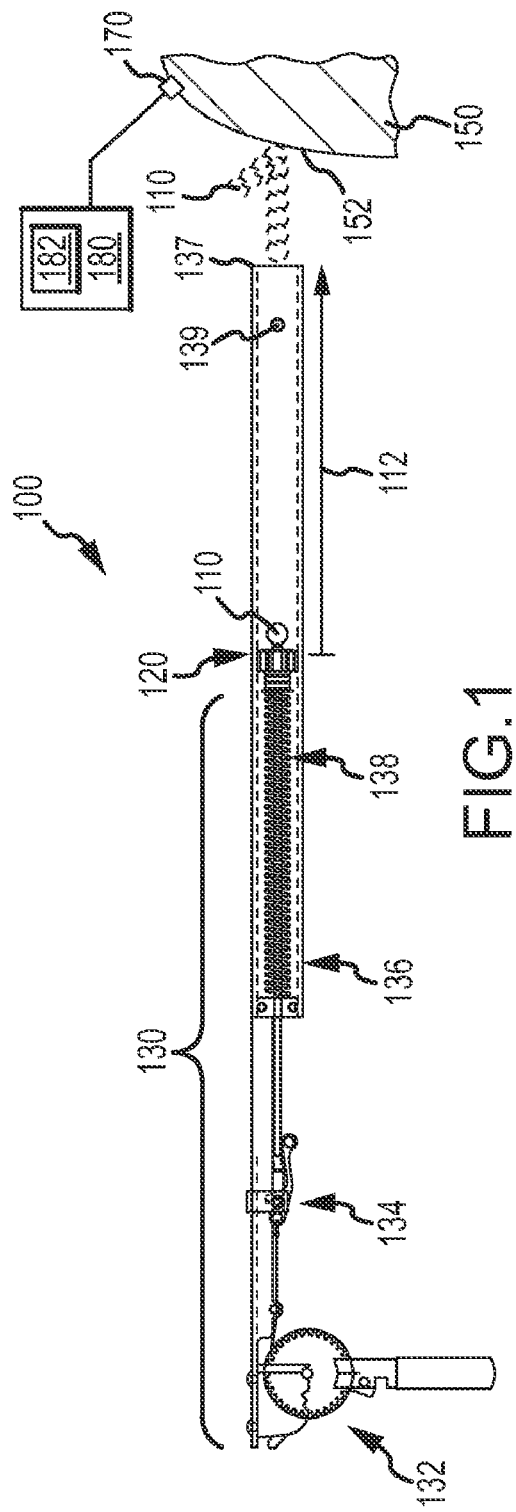
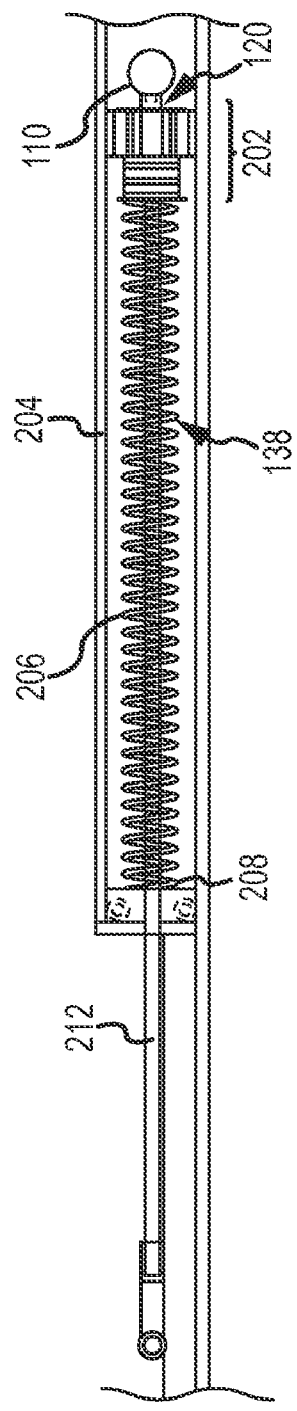

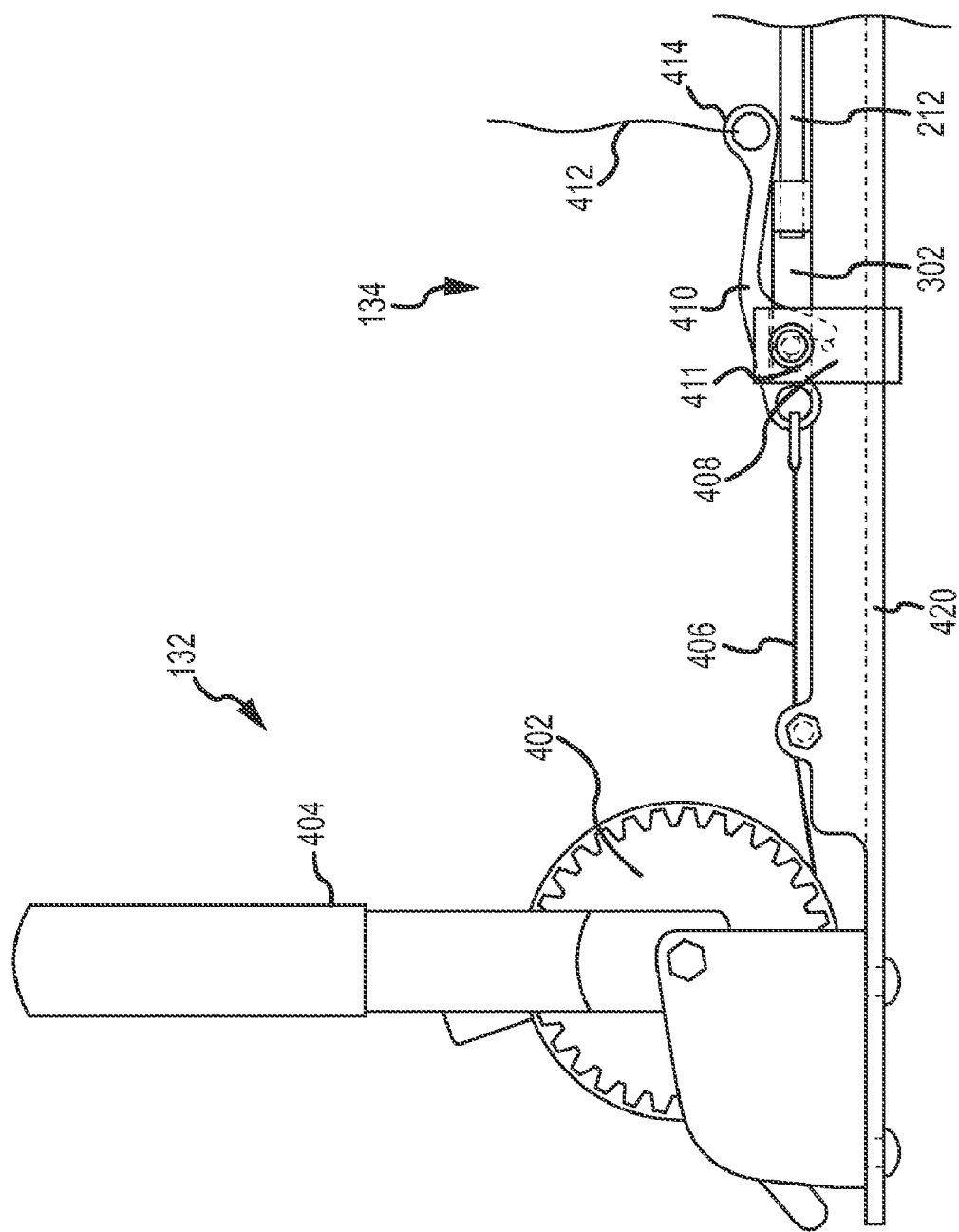

METHODS AND APPARATUS FOR HIGH FREQUENCY IMPACT TESTING

GOVERNMENT RIGHTS

This invention was made with United States Government support under Contract number HQ0006-01-C-0001. The United States Government has certain rights in this invention.

TECHNICAL FIELD

The present invention generally relates to structural testing, and more particularly relates to high frequency testing of a structure via surface impact.

BACKGROUND

It is often desirable to test a component or structure to a known shock transient or known shock response spectrum (SRS). The SRS is a method which depicts the transient acceleration (in G's) of the test structure as a function of frequency.

Known methods of performing shock testing with high frequency, very short duration are unsatisfactory in a number of respects. For example, one method involves dropping a large steel ball onto a test structure from a known height. This method can create the desired high frequency response, but often greatly over-tests the low frequency response. It is also limited by the drop height and the terminal velocity of the ball. Conversely, if the low frequency is tested within the desired limits, the high frequency tends to be under-tested.

Another method involves using a gas-filled chamber to project an impacting projectile. This method is undesirable because it is difficult to carefully control the impact force, and therefore the repeatability of the test is insufficient.

A third method involves the use of an explosive charge, or pyrotechnic testing. This method is extremely hard to control and requires specialized test personnel and laboratories. Furthermore, Pyrotechnic testing typically results in over-testing of the component or structure.

Accordingly, it is desirable to provide simple and repeatable methods for performing high frequency shock testing various structures. Other desirable features and characteristics of the present invention will become apparent from the subsequent detailed description and the appended claims, taken in conjunction with the accompanying drawings and the foregoing technical field and background.

BRIEF SUMMARY

In accordance with one embodiment of the present invention, an impact testing system for determining the shock response of a test structure includes: a mass (e.g., a spherical steel ball); a potential energy storage system (e.g., a spring-loaded mechanism) configured to store mechanical energy and, upon actuation, release the stored mechanical energy in the form of kinetic energy; and a hold-and-release mechanism (such as a permanent magnet) configured to releasably couple the mass to the potential energy storage system and impart linear momentum to the mass in connection with the kinetic energy such that the mass impinges upon the test structure. The shock response can then be determined and displayed to a user.

An exemplary method for impact testing a test structure includes positioning a potential energy storage system adjacent to a surface of the test structure; coupling at least one sensor to a surface of the test structure; coupling a mass to the potential energy storage system; activating the potential energy storage system to store a predetermined amount of mechanical energy; actuating the potential energy storage system to release the stored mechanical energy in the form of kinetic energy and impart linear momentum to the mass such that the mass decouples from the potential energy storage system and impinges upon the test structure; measuring the shock response of the test structure via the at least one sensor; and displaying a visual representation of the test results, e.g., a shock response spectrum.

A high-frequency impact device in accordance with another embodiment includes: a plunger assembly coupled to and coaxial with a linear spring; a winch assembly configured to adjustably retract the plunger assembly and compress the linear spring; a latch mechanism coupled between the winch assembly and plunger assembly and configured to selectably release the plunger from the winch assembly; and a magnetic hold-and-release mechanism coupled to one end of the plunger assembly and configured to releasably hold a metallic sphere.

BRIEF DESCRIPTION OF THE DRAWINGS

A more complete understanding of the present invention may be derived by referring to the detailed description and claims when considered in conjunction with the following figures, wherein like reference numbers refer to similar elements throughout the figures.

FIG. 1 is a side view of an impact tester in accordance with one embodiment;

FIG. 2 is a close-up of various components illustrated in FIG. 1;

FIG. 4 is a close-up of exemplary winch and latch assemblies as shown in FIG. 1.

DETAILED DESCRIPTION

Figure 3:
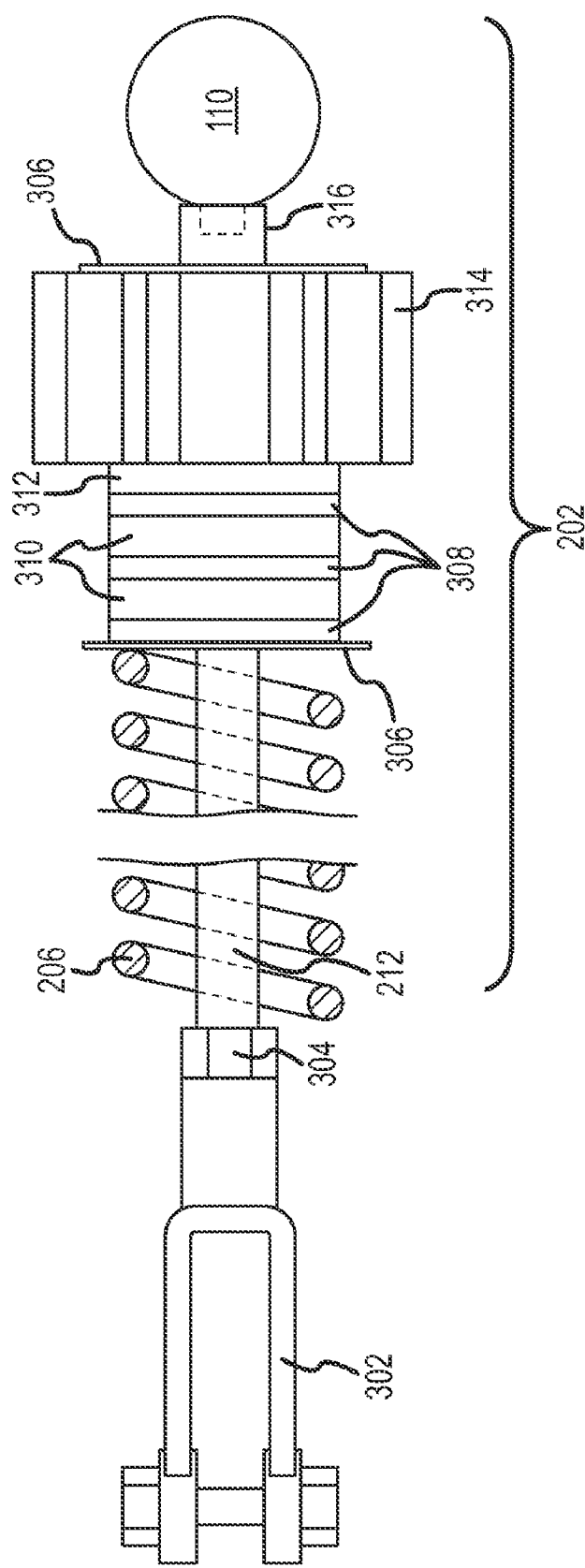
FIG. 3 is a close-up of various plunger assembly components illustrated in FIG. 1.

The following discussion generally relates to improved methods and apparatus for impact testing of structures, such as spacecraft or missile structures, using a relatively small projectile that impinges on the structure's surface in a controllable and repeatable manner. In that regard, the following detailed description is merely illustrative in nature and is not intended to limit the invention or the application and uses of the invention. Furthermore, there is no intention to be bound by any expressed or implied theory presented in the preceding technical field, background, brief summary or the following detailed description. For the purposes of conciseness, conventional techniques and principles related to mechanical testing, dynamics, data acquisition, and the like need not, and are not, described in detail herein.

Referring now to FIG. 1, a high frequency impact testing system (HFIT, or simply "impact testing system") 100 is configured to determine the shock response of a test structure 150, and generally includes a mass (or "ball") 110, a hold-and-release mechanism 120, and a potential energy storage system or assembly 130. Without loss of generality, mass 110 will be referred to herein as a spherical ball; however, the present invention is not so limited.

Potential energy storage system 130 is configured to store mechanical energy and, upon actuation, release the stored mechanical energy in the form of kinetic energy, thereby imparting linear momentum to ball 110 such that it impinges upon a surface 152 of test structure 150. Assembly 130 may have any number of springs, torsion members, and the like capable of storing and releasing the desired amount of potential energy. In an illustrated embodiment, a linear spring is used in conjunction with winch and latch assemblies, as described in further detail below.

Hold-and-release mechanism 120 is configured to releasably couple ball 110 to potential energy storage system 130. That is, mechanism 120 is capable of holding ball 110 in place prior to the testing event, but releases ball 110 after the potential energy is released in the form of kinetic energy such that ball 110 becomes a projectile aimed at test structure 150 in the direction of a translation axis 112. As described in further detail below, in one embodiment mechanism 120 includes one or more permanent magnets of sufficient strength to hold a metallic (e.g., steel) ball 110 in place.

At least one sensor 170 is coupled to test structure 150 to measure its response to impinging ball 110. Sensor 170 (e.g., a standard acceleration sensor) is suitably coupled to processor 180 (e.g., a general purpose computer, controller, or the like), which has an associated display 182. Processor 180, via any combination of hardware and software, is configured to determine the shock response of the test structure via signals from sensor 170 and then provide the results to display 182 for inspection by a user. In one embodiment, display 182 includes a shock response spectrum (SRS) associated with the test event.

The mass and size of ball 110 may be selected in accordance with the desired frequency range of the particular testing regimen and the nature of test structure 150, as is known in the art. In one embodiment, for example, ball 110 is a substantially spherical steel ball having a diameter ranging from approximately 1.0 to 1.25 inches. Generally, a hardened steel ball is desirable in order to transfer the maximum high frequency content; however, a lower hardness steel, or other magnetic material—e.g., iron—may be employed to customize the frequency content of the impact.

In the illustrated embodiment, potential energy storage system 130 generally includes a spring-loaded plunger assembly 138 that is loaded via a winch assembly 132 and is actuated using a latch assembly 134. Ball 110 is held in place by hold-and-release mechanism 120, and when plunger assembly 138 is released (via latch assembly 134), plunger assembly 138 translates along axis 112 until it reaches the extent of its travel, at which time ball 110 is released as a projectile toward its target (i.e., surface 152 of structure 150). Note that while the illustrations show a generally horizontal orientation for impact tester 100, in practice the assembly can be oriented and positioned in any desired manner. Various other conventional structural components may be used to keep tester 100 in place, but for the purposes of clarity are not illustrated in the drawings.

FIG. 2 depicts a close-up of various components shown in FIG. 1. More particularly, spring 206 fits around a plunger rod (or "rod") 212, both of which are coaxially positioned within a tube (e.g., a rectilinear cross-section tube) 204 such that, when rod 212 is retracted (moved to the left in the figure), spring 206 compresses, storing energy. A plunger end subassembly 202 is located at one end of spring 206. When rod 212 is released, a stop attached to rod 212 contacts end cap 208 at the end of its travel, causing ball 110 to be released. The velocity of ball 110 at release can be adjusted by adjusting the compression distance of spring 206 and/or by selecting a different spring constant (e.g., size, material) for spring 206. In one embodiment, for example, a spring force of 9.0 lbs/inch is desirable. In alternate embodiments, multiple springs 206 may be used. In the interest of safety, a lockout pin may be placed in a corresponding pair of holes on opposite sides of tube 204 (e.g., hole 139 in FIG. 1).

Referring now to FIG. 3 together with FIG. 1, plunger end sub-assembly 202 coupled to rod 212 generally includes one or more metal washers 306, one or more rubber washers 308, one or more magnets 310, plunger 312, guide (e.g., a Teflon guide) 314, and cap screw 316.

Plunger end sub-assembly 202 has three primary functions. First, it provides a low-friction guide for projecting ball 110 inside tube 204. Second, it releasably holds ball 110 in place via magnets 310. Third, it captures one end of spring 206. In one embodiment, guide 314 consists of a Teflon material and has eight minimal tube contact points along the inner surface of tube 204, such that it provides a clearance to allow air to pass through during actuation.

Plunger 312 is preferably steel or another metallic material that can transmit the magnetic field from magnets 310 to ball 110. Magnets 310 are captured between plunger 312 and washer 306, and are sandwiched between rubber washers 308. The rubber washers 308 serve as a cushion to prevent shock damage during actuation. The magnetic force is preferably sufficient to hold the ball in place prior to actuation without significantly reducing the escape velocity of the ball. An internal hex feature on the head of cap screw 316 provides a cup for receiving ball 110.

Rod 212, which may, for example, comprise a suitable aluminum alloy, is coupled to jam nut 304 of clevis 302. Clevis 302 allows the plunger assembly to be attached to the winch assembly.

Referring to FIG. 4 and FIG. 1, winch assembly 132 includes a conventional winch 402 and handle 404, as is known in the art. A belt 406 (e.g., a nylon belt) is coupled between winch 402 and latch assembly 134. A support structure 420 is provided for stabilizing the components.

Winch 402 and handle 404 provide the mechanical leverage to spring load plunger assembly 138. During operation, belt 406 is lengthened, allowing latch 410 to connect with clevis 302. Winch 402 is then ratcheted to compress spring 206 to the desired position. A slotted rectangular retaining clip 408 is secured over clevis 302 and latch 410. Clip 408 keeps plunger rod 212 from deflecting during release of latch 410 from clevis 302.

A pull cord 412 or other actuation component is coupled to end 114 of latch 410. When pull cord 412 is actuated, latch 410 pivots with respect to clip 408, thereby releasing clevis 302 from detent or notch 411 in latch 410. Rod 212 (and consequently ball 110) then travels quickly under the force of spring 206 until the end of its travel, at which time ball 110 is released toward its target.

While at least one example embodiment has been presented in the foregoing detailed description, it should be appreciated that a vast number of variations exist. It should also be appreciated that the example embodiment or embodiments described herein are not intended to limit the scope, applicability, or configuration of the invention in any way. Rather, the foregoing detailed description will provide those skilled in the art with a convenient and edifying road map for implementing the described embodiment or embodiments. It should be understood that various changes can be made in the function and arrangement of elements without departing from the scope of the invention and the legal equivalents thereof.

What is claimed is:

1. An impact testing system for determining the shock response of a test structure, comprising:
 a mass;
 a potential energy storage system configured to store mechanical energy and, upon actuation, release the stored mechanical energy in the form of kinetic energy; and a hold-and-release mechanism configured to releasably couple the mass to the potential energy storage and impart linear motion to the mass in connection with the kinetic energy such that the mass impinges upon the test structure;

at least one sensor coupled to the test structure remote from the mass;

a processor coupled to the at least one sensor and configured to determine the shock response of the test structure resulting from the mass impinging upon the test structure; and a display coupled to the processor for providing a visual representation of the shock response.

2. The impact testing system of claim 1, wherein the at least one sensor is an acceleration sensor.

3. The impact testing system of claim 1, wherein the mass is a substantially spherical ball.

4. The impact testing system of claim 3, wherein the mass comprises steel.

5. The impact testing system of claim 4, wherein the mass has a diameter between approximately 1.0 and 1.25 inches.

6. The impact testing system of claim 1, wherein the hold-and-release mechanism comprises a permanent magnet configured to produce a magnetic field for releasably holding the mass.

7. The impact testing system of claim 1, wherein the potential energy storage system comprises a spring-loaded mechanism.

8. An impact testing system for determining the shock response of a test structure, comprising:
 a mass;
 a potential energy storage system configured to store mechanical energy and, upon actuation, release the stored mechanical energy in the form of kinetic energy; and
 a hold-and-release mechanism configured to releasably couple the mass to the potential energy storage and impart linear momentum to the mass in connection with the kinetic energy such that the mass impinges upon the test structure;
wherein the spring-loaded mechanism comprises:
 a plunger assembly;
 a spring coupled to the plunger assembly;
 a winch assembly coupled to the plunger assembly and configured to adjustably compress the spring; and
 a latch assembly coupled to the winch assembly, the latch assembly configured to releasably engage the plunger assembly; and
 wherein the potential energy storage system comprises a spring-loaded mechanism.

9. A method for utilizing a potential energy storage system, a mass coupled to the potential energy storage system, and a remote sensor for impact testing a test structure, comprising:
 positioning the potential energy storage system adjacent to a surface of the test structure;
 coupling the sensor to a surface of the test structure;
 coupling a mass to the potential energy storage system, wherein the sensor is remote from the mass;
 activating the potential energy storage system to store a predetermined amount of mechanical energy;
 actuating the potential energy storage system to release the stored mechanical energy in the form of kinetic energy and to impart linear momentum to the mass such that the mass decouples from the potential energy storage system and impinges upon the test structure;
 measuring the shock response of the test structure via the one sensor; and
 displaying a visual representation of the shock response.

10. The method of claim 9, wherein the displaying step includes displaying a shock response spectrum.

11. The method of claim 9, wherein the mass is a substantially spherical ball.

12. The method of claim 11, wherein the mass comprises steel and has a diameter of between approximately 1.0 and 1.25 inches.

13. The method of claim 9, wherein the mass is releasably coupled to the potential energy storage system via a magnetic field.

14. A method for impact testing a test structure, comprising:
 positioning a potential energy storage system adjacent to a surface of the test structure;
 coupling at least one sensor to a surface of the test structure;
 coupling a mass to the potential energy storage system;
 activating the potential energy storage system to store a predetermined amount of mechanical energy;
 actuating the potential energy storage system to release the stored mechanical energy in the form of kinetic energy and impart linear momentum to the mass such that the mass decouples from the potential energy storage system and impinges upon the test structure;
 measuring the shock response of the test structure via the at least one sensor; and
 displaying a visual representation of the shock response;
 wherein the activating step includes adjusting a winch assembly coupled to a plunger assembly to compress a spring.

15. The method of claim 14, wherein the actuating step includes:
 activating a latch assembly coupled between the winch assembly and the plunger assembly.

16. A high-frequency impact device comprising:
 a plunger assembly coupled to and coaxial with a linear spring;
 a winch assembly configured to adjustably retract the plunger assembly and compress the linear spring;
 a latch mechanism coupled between the winch assembly and plunger assembly and configured to selectably release the plunger from the winch assembly; and
 a magnetic hold-and-release mechanism coupled to one end of the plunger assembly and configured to releasably hold a metallic sphere.

17. The high-frequency impact device of claim 16, further comprising a tube coaxial with the plunger assembly and coupled to one end of the spring via an end cap.

18. The high-frequency impact device of claim 17, further including a guide at one end of the plunger assembly and configured to contact an inner surface of the tube.

19. The high-frequency impact device of claim 17, wherein the winch assembly includes a belt coupled to the latch mechanism.

* * * * *

UNITED STATES PATENT AND TRADEMARK OFFICE
CERTIFICATE OF CORRECTION

| | | |
|---|---|---|
| PATENT NO. | : 8,001,826 B2 | Page 1 of 1 |
| APPLICATION NO. | : 12/472124 | |
| DATED | : August 23, 2011 | |
| INVENTOR(S) | : Dwight Schwarz and Mark J. Kocan | |

It is certified that error appears in the above-identified patent and that said Letters Patent is hereby corrected as shown below:

Column 6, line 1 claim 9 – the word "and" should be deleted

Column 6, line 5 claim 9 – the word "one" should be deleted

Signed and Sealed this
Eighth Day of November, 2011

David J. Kappos
*Director of the United States Patent and Trademark Office*